US005710165A

United States Patent [19]
Kapin et al.

[11] Patent Number: 5,710,165
[45] Date of Patent: Jan. 20, 1998

[54] USE OF POLYAMINE ANTAGONISTS FOR THE TREATMENT OF GLAUCOMA

[75] Inventors: Michael A. Kapin, Arlington; Louis Desantis, Jr., Fort Worth, both of Tex.; Salomon Langer, Paris, France

[73] Assignee: Synthelabo, Cedex, France

[21] Appl. No.: 271,290

[22] Filed: Jul. 6, 1994

[51] Int. Cl.$^6$ .......................... A01N 43/40; A61K 31/445
[52] U.S. Cl. ........................................ 514/317; 514/913
[58] Field of Search ................................ 514/317, 337, 514/913

[56] References Cited

U.S. PATENT DOCUMENTS

| | | |
|---|---|---|
| 4,690,931 | 9/1987 | Wick et al. |
| 5,382,576 | 1/1995 | Schoenwald et al. ............ 514/913 X |
| 5,397,797 | 3/1995 | Ueno ................................ 514/913 X |
| 5,405,846 | 4/1995 | Ueno ................................ 514/913 X |

FOREIGN PATENT DOCUMENTS

WO 94/13275  6/1994  WIPO.

OTHER PUBLICATIONS

Tung et al., "A quantitative analysis of the effects of excitatory neurotoxins on retinal ganglion cells in the chick," *Visual Neurosci.*, 4:217–223 (1990).

Sisk et al., "Histological changes in the inner retina of albino rats following intravitreal injection of monosodium L–glutamate," *Graefe's Arch. Clin. Exp. Ophthalmol.*, 223:250–258 (1985).

Siliprandi et al., "N–methyl–D–aspartate–induced neurotoxicity in the adult rat retina," *Visual Neurosci.*, 8:567–573 (1992).

Reif–Lehrer et al., "Effects of monosodium glutamate on chick embryo retina in culture," *Invest. Ophthalmol. Vis. Sci.*, 14(2):114–124 (1975).

Blank, J.C., "Effects of monosodium glutamate on the isolated retina of the chick embryo as a function of age: A morphological study," *Exp. Eye Res.*, 32:105–124 (1981).

Olney et al., "The role of specific ions in glutamate neurotoxicity," *Neurosci. Lett.*, 65:65–71 (1986).

Olney et al., "The anti–excitotoxic effects of certain anesthetics, analgesics and sedative–hypnotics," *Neurosci. Lett.*, 68:29–34 (1986).

Price et al., "CNQX potently and selectively blocks kainate excitotoxicity in the chick embryo retina," *Soc. Neurosci. Abst.*, 14:418 (1988).

David et al., "Involvement of excitatory neurotransmitters in the damage produced in chick embryo retinas by anoxia and extracellular high potassium," *Exp. Eye Res.*, 46:657–662 (1988).

Caprioli et al., "Large retinal ganglion cells are more susceptible to excitotoxic and hypoxic injury than small cells," *Invest. Ophthalmol. Vis. Sci.*, 34(Suppl.): 1429 (1993).

Cummins et al., "Electrophysiology of cultured retinal ganglion cells to investigate basic mechanics of damage," *Glaucoma Update IV*, 59–65 (1991).

Sucher et al., "N–methyl–D–aspartate antagonists prevent kainate neurotoxicity in rat retinal ganglion cells in vitro," *J. Neurosci*, 11(4):966–971 (1991).

Massey, S., "Cell types using glutamate as neurotransmitter in the vertebrate retina," N.N. Osborne and G.J. Chader (Eds.) *Progress in Retinal Research*, Ch. 9, Pergammon Press:Oxford, 339–425 (1990).

Miller et al., "Excitatory amino acid receptors in the vertebrate retina," *Retinal Transmitters and Modulators: Models for the Brain*, (W.W. Morgan, Ed.) CRC Press, Inc., Boca Raton, II:123–160 (1985).

Zeevalk et al., "Action of the anti–ischemic agent ifenprodil on N–methyl–D–aspartate and kainatemediated excitotoxicity," *Brain Res.*, 522:135–139 (1990).

Ornstein et al., "Antagonists of the NMDA receptor complex," *DN&P*, 7(1):5–12 (1994).

Lipton, S.A., "Prospects for clinically tolerated NMDA antagonists: open–channel blockers and alternative redox states of nitric oxide," *TINS*, 16(12):527–532 (1993).

Beal, M.F., "Mechanisms of excitotoxicity in neurologic diseases," *FASEB J.*, 6:3338–3344 (1992).

Choi, D.W., "Excitotoxic cell death," *J. Neurobiol.*, 23:1261–1276 (1992).

Sattayasai et al., "Morphology of quisqualate–induced neurotoxicity in the chicken retina," *Invest. Ophthalmol. Vis. Sci.*, 28:106–117 (1987).

*Quest Med.*, 33(2–3):75–85 (1980).

Primary Examiner—Paul F. Shaver
Attorney, Agent, or Firm—Sally Yeager

[57] ABSTRACT

Polyamine antagonists are found to be effective in preventing or reducing visual field loss associated with glaucoma. Especially preferred are certain 1-phenyl-2-piperidinoalkanol derivatives, such as eliprodil and ifenprodil.

3 Claims, 2 Drawing Sheets

USE OF POLYAMINE ANTAGONISTS FOR THE TREATMENT OF GLAUCOMA

BACKGROUND OF THE INVENTION

The present invention relates generally to the field of ophthalmology. In particular, the invention relates to the use of eliprodil and related polyamine antagonists to preserve visual field and function by preventing or reducing optic nerve head and retinal damage related to glaucoma in mammalian subjects.

Although the underlying causes of glaucoma are not understood at this time, glaucoma is characterized by damage to the optic nerve, accompanied by a decrease in the normal visual field. One early warning sign of possible glaucomatous visual field loss is elevated intraocular pressure ("IOP"). In fact, glaucoma has historically been treated by medically and/or surgically lowering elevated IOP; however, elevated IOP does not always result in the occurrence of visual field loss, and visual field loss may occur at levels of IOP which are considered within the normal range. Thus, factors other than IOP may play a role in determining the occurrence of visual field loss. Degeneration involving retinal ganglion cells may be related to ischemia or mechanical distortion of the nerve fibers as they exit through the optic nerve head or from pathological perturbations of the retina.

There has been a growing interest in retinal dysfunction as a contributor to the glaucomatous process. Retinal dysfunction, and hence pathology, may be related to ischemia or excitotoxicity. Excitotoxicity is neuronal injury due to excessive excitatory amino acid ("EAA") stimulation. In the inner retina, glutamate is the major EAA that permits the bipolar and amacrine cells to communicate with the ganglion cell. In the central nervous system, excitotoxicity results from hypoxia, ischemia, hypoglycemia or trauma. (See, for example, Beal, M. F., "Mechanisms of excitotoxicity in neurologic diseases," *FASEB J.*, 6:3338–3344 (1992); and Choi, D. W., "Excitotoxic cell death," *J. Neurobiol.*, 23:1261–1276 (1992).) Toxicity to the inner retina has been observed following intravitreal injection of EAAs following application of EAAs to the isolated animal retina or from exogenously applied glutamate to retinal ganglion cells in culture. See generally, Sattayasai, et al., "Morphology of quisqualate-induced neurotoxicity in the chicken retina," *Invest. Ophthalmol. Vis. Sci.*, 28:106–117 (1987); Tung et al., "A quantitative analysis of the effects of excitatory neurotoxins on retinal ganglion cells in the chick, *Visual Neurosci.*, 4:217–223 (1990); Sisk et al., "Histological changes in the inner retina of albino rats following intravitreal injection of monosodium L-glutamate," *Graefe's Arch. Clin. Exp. Ophthalmol.*, 223:250–258 (1985); Siliprandi et al., "N-methyl-D-aspartate-induced neurotoxicity in the adult rat retina," *Visual Neurosci.*, 8:567–573 (1992); Reif-Lehrer et al., "Effects of monosodium glutamate on chick embryo retina in culture," *Invest. Ophthalmol. Vis. Sci.*, 14(2):114–124 (1975); Blanks, J. C., "Effects of monosodium glutamate on the isolated retina of the chick embryo as a function of age: A morphological study," *Exp. Eye Res.*, 32:105–124 (1981 ); Olney et al., "The role of specific ions in glutamate neurotoxicity," *Neurosci. Lett.*, 65:65–71 (1986); Olney et al., "The antiexcitotoxic effects of certain anesthetics, analgesics and sedative-hypnotics," *Neurosci. Lett* 68:29–34 (1986); Price et al., "CNQX potently and selectively blocks kainate excitotoxicity in the chick embryo retina," *Soc. Neurosci. Abst.*, 14:418 (1988); David et al., "Involvement of excitatory neurotransmitters in the damage produced in chick embryo retinas by anoxia and extracellular high potassium," *Exp. Eye Res.*, 46:657–662 (1988); Caprioli et al., "Large retinal ganglion cells are more susceptible to excitotoxic and hypoxic injury than small cells *Invest. Ophthalmol. Vis. Sci.*, 34(Suppl):1429 (1993); Cummins et al., "Electrophysiology of cultured retinal ganglion cells to investigate basic mechanics of damage," *Glaucoma Update IV,* 59–65 (1991 ); and Sucher et al., "N-methyl-D-aspartate antagonists prevent kainate neurotoxicity in rat retinal ganglion cells in vitro," *J. Neurosci.*, 11(4):966–971 (1991).

EAA receptors have been characterized as metabotropic or ionotropic. Activation of a metabotropic receptor affects cellular processes via G-proteins; whereas ionotropic receptors affect the translocation of mono- and divalent cations across the cell membrane. There are at least three ionotropic receptors that have been named for the agonist that preferentially stimulates the receptor. These receptors have been classified as: N-methyl-D-aspartate (NMDA); kainate; and AMPA (2-amino-3-(3-hydroxy-5-methylisoxazol-4-yl) propanoic acid). These EAA receptors are differentially distributed to specific cells in the retina. (See, for example, Massey, S., "Cell types using glutamate as a neurotransmitter in the vertebrate retina," N. N. Osborne and G. J. Chader (Eds.) *Progress in Retinal Research,* Ch. 9, Pergammon Press: Oxford, 399–425 (1990); and Miller et al., "Excitatory amino acid receptors in the vertebrate retina," in *Retinal Transmitters and Modulators: Models for the Brain,* (W. W. Morgan, Ed.) CRC Press, Inc., Boca Raton, II:123–160 (1985).) The localization of such receptors would account for the pathologies associated with glaucoma or inner retinal ischemia. For example, death of the retinal ganglion cell has to a large part been attributed to the NMDA receptor. (See, for example, Sucher et al., "N-methyl-D-aspartate antagonists prevent kainate neurotoxicity in retinal ganglion cells in vitro," *J. Neurosci.*, 11(4):966–971 (1991).). Thus, antagonists of the NMDA receptor are neuroprotective; however, not all antagonists of the diversely distributed EAA receptors are neuroprotective to the inner retina through antagonism of the NMDA receptor, Zeevalk et al., "Action of the anti-ischemic agent ifenprodil on N-methyl-D-aspartate and kainate-mediated excitotoxicity," *Brain Res.*, 522:135–139 (1990)), and many of these EAA antagonists have significant CNS side-effects and are therefore not suitable for treating these degenerative diseases of the eye.

SUMMARY OF THE INVENTION

Eliprodil and related polyamine antagonists are a specific subset of EAA antagonists which binds to an unique location on the NMDA receptor. It has now been found that these compounds do not produce the CNS side-effects that are characteristic of other EAA antagonists.

The present invention provides a new method for the treatment of glaucoma by administration of a neuroprotectant such as eliprodil or related polyamine antagonists. The present invention also provides for the treatment of retinopathy caused by ischemia or excitotoxicity. Administration of drug is achieved through those routes capable of treating the back of the eye. This would encompass administrations of the drug through a systemic route (e.g., oral, subcutaneous, intravenous, transnasal, buccal, or transdermal) or the potential delivery of the drug via a topical ocular route, in a periocular injection, an intravitreal implant, or via iontophoresis.

DETAILED DESCRIPTION OF THE INVENTION

Figure 1:
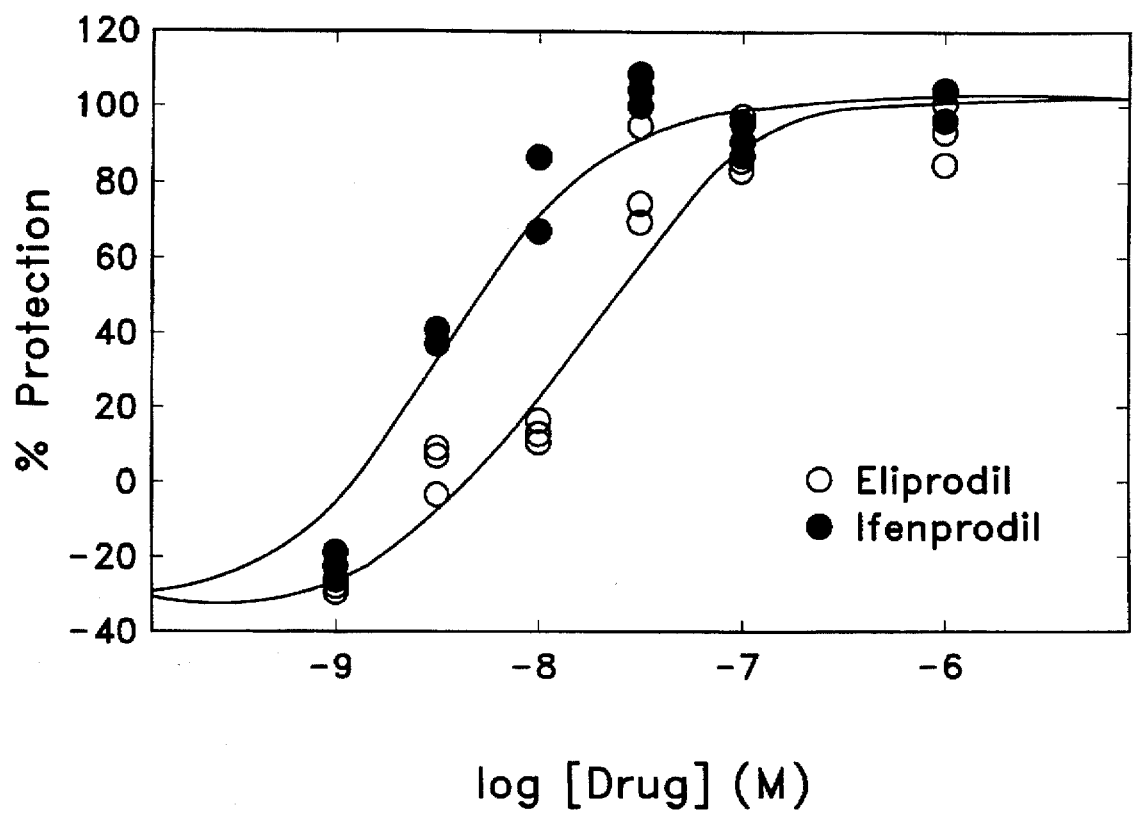
FIG. 1 is a graph illustrating dose response curves of eliprodil and ifenprodil for their protective actions against glutamate-induced death of the Y79 cells. Each symbol represents datum obtained from a single sample. Protection ranges for 0% to 100%, where 0% indicates no protection and 100% indicates cell survival equivalent to that of control samples without glutamate treatment.

Eliprodil and other polyamine antagonists are one of four classes of NMDA antagonists. (See, for example, Ornstein et al., "Antagonists of the NMDA receptor complex," *DN&P,* 7(1):5–12 (1994).) The classes include the competitive antagonists which antagonize the glutamate recognition site, non-competitive channel blockers; glycine antagonists and polyamine antagonists, the latter two modulate the glutamate response on the receptor. The glycine and polyamine modulatory sites are distinct. As aforementioned, antagonists of EAA receptors have been used in the CNS to prevent neuronal injury in animal models of ischemia, hypoglycemia and trauma. Pharmacologically, competitive and non-competitive antagonists suffer from their inability to cross the blood-brain barrier or that they produce undesirable (psychotomimetic) side effects. Unlike other NMDA antagonists, the polyamine antagonists such as eliprodil partition across the blood-brain barrier and produce their actions at a modulatory site without side-effects typical of non-competitive antagonists. (See, for example, Lipton, S. A., "Prospects for clinically tolerated NMDA antagonists: open-channel blockers and alternative redox states of nitric oxide." *TINS,* 16(12): 527–532 (1993).)

Particularly preferred polyamine antagonists are certain 1-phenyl-2-piperidinoalkanol derivatives of formula (I), below:

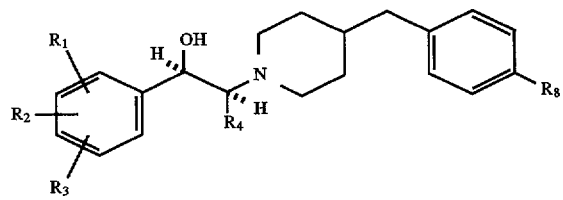

wherein:

$R_1$ represents a hydrogen atom, a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4-position and $R_3$ represents a hydrogen atom, $R_1$ may also represent a hydroxymethyl group, a carbamoyl group or an alkoxycarbonyl group having from 1 to 4 carbon atoms in the alkoxy part, $R_2$ represents a hydrogen atom, a halogen atom, an alkyl group having from 1 to 4 carbon atoms, a hydroxyl group or an alkoxy group having from 1 to 4 carbon atoms, $R_3$ represents a hydrogen atom or an alkyl group having from 1 to 4 carbon atoms, $R_4$ represents an alkyl group having from 1 to 4 carbon atoms, in which case the compounds are in the (±)-erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical, and pharmaceutically acceptable acid addition salts thereof.

The compounds of formula (I) above are described in U.S. Pat. No. 4,690,931 (Wick et al.); however, there is no mention in that patent of ophthalmic indications for such compounds. Wick et al. also describe methods for synthesizing such compounds. The entire contents of U.S. Pat. No. 4,690,931 are incorporated herein by reference.

The most preferred compounds are: 2-[4-(4-fluorobenzyl)-piperidino]-1-(4-chlorophenyl)-ethanol, also known as eliprodil; 2-(4-benzylpiperidino)-1-(4-hydroxyphenyl)-propanol, also known as ifenprodil; or a pharmaceutically acceptable salt thereof. The structures of eliprodil and ifenprodil are shown below.

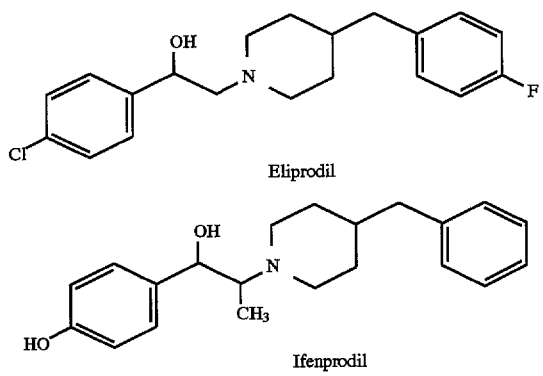

In general, the polyamine antagonists useful in the present invention will be administered orally. Daily dosage of these compounds will range between about 0.1 and about 500 milligrams (mg), preferably between about 5 and about 100 mg. While at the present time there are no effective methods for local administration to the back of the eye, it is contemplated that such methods will be developed. If local administration of these compounds becomes feasible, it is expected that the dosage will range between about 0.1 and about 500 mg, preferably between about 5 and about 100 mg. An aqueous composition will generally contain between about 0.1 and about 10 percent by weight (wt %) of the active, preferably between about 1 and about 5 wt %.

The following example is presented to illustrate further various aspects of the present invention, but is not intended to limit the scope of the invention in any respect.

EXAMPLE

A study was conducted to corroborate the neuroprotective effects of the polyamine antagonists, eliprodil and ifenprodil.

Human retinoblastoma (Y79) cells were cultured in Dulbecco's modified Eagle's medium supplemented with 4 mM L-glutamine and 50 µg/mL gentamicin at 37° C. in humidified 95% air (5% $CO_2$). During the day of study, cells were centrifuged and resuspended in Buffer A (NaCl 125 mM, KCl 5 mM, $CaCl_2$ 1.8 mM, $MgCl_2$ 2 mM, $NaH_2PO_4$ 0.5 mM, $NaHCO_3$ 5 mM, Hepes 10 mM, dextrose 10 mM, pH=7.2 at room temperature) into a cell density of 1.5 to $2 \times 10^5$ cells/mL. Eliprodil or ifenprodil at concentrations indicated was added to 0.4 ml of cell suspension and the mixture incubated for 30 min at room temperature. L-Glutamate (final concentration=1 mM) was then added and the cell mixture incubated at room temperature for 3 hours. At the end of this incubation period, 0.04 mL of 0.33% neutral red reagent was added to each sample and incubated for another 2 hours at room temperature. The cells were then centrifuged, washed with 1 mL of phosphate-buffered saline and centrifuged again. The cell pellets were then solubilized with 0.5 mL of solubilization buffer (acetic acid 1%, ethanol 50%). Optical density of 570 nm of the cell lysate was quantified and recorded. The optical density is proportional to the number of surviving cells.

Figure 2:
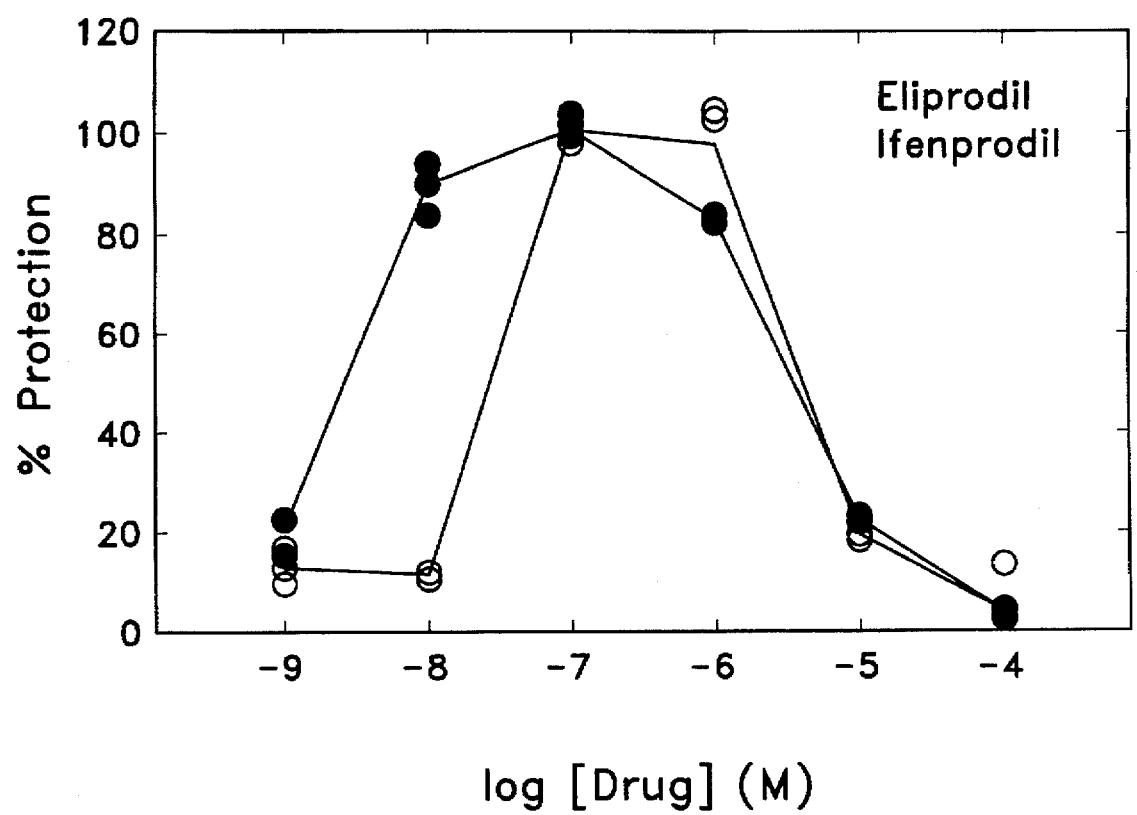
FIG. 2 is a graph illustrating expanded dose response curves of eliprodil and ifenprodil. At concentrations higher than 1 µM, both eliprodil and ifenprodil were less protective against the toxicity of glutamate.

The results of the study are presented in FIGS. 1 and 2. Both eliprodil and ifenprodil gave bell-shaped dose responses, with 100 nM and 1 µM being the most protective doses for glutamate (1 mM)-induced toxicity.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for treating glaucoma, comprising administering to an affected person an amount of eliprodil effective to reduce visual field loss.

2. The method of claim 1, wherein the affected person is administered between about 0.1 and about 500 mg of eliprodil on a daily basis.

3. The method of claim 2, wherein the affected person is administered between about 5 and about 100 mg of eliprodil on a daily basis.

* * * * *